US00PP19513P2

(12) United States Plant Patent
Bunker

(10) Patent No.: US PP19,513 P2
(45) Date of Patent: Dec. 2, 2008

(54) ***BRACTEANTHA* PLANT NAMED 'FLOBRASAT'**

(50) Latin Name: *Bracteantha bracteata*
Varietal Denomination: FLOBRASAT

(75) Inventor: Kerry V. Bunker, Redland Bay (AU)

(73) Assignee: Floreta Intellectual Property Pty. Ltd. (AU)

( * ) Notice: Subject to any disclaimer, the term of this patent is extended or adjusted under 35 U.S.C. 154(b) by 0 days.

(21) Appl. No.: 11/879,596

(22) Filed: Jul. 18, 2007

(51) Int. Cl.
*A01H 5/00* (2006.01)

(52) U.S. Cl. ..... Plt./359

(58) Field of Classification Search ..... Plt./359
See application file for complete search history.

*Primary Examiner*—Kent L. Bell
*Assistant Examiner*—June Hwu

(57) ABSTRACT

A new and distinct cultivar of *Bracteantha* plant named 'FLOBRASAT', particularly characterized by its clear white inflorescences which are held above the foliage on long peduncles, compact plant habit, many inflorescences per plant, early flowering, and narrow leaf width.

1 Drawing Sheet

The present invention relates to a new and distinct cultivar of *Bracteantha* plant, botanically known as *Bracteantha bracteata* and referred to by the variety denomination 'FLOBRASAT'. The genus and species were formerly known as *Helichrysum bracteatum,* and *Bracteantha bracteata* is synonymous with the more recent botanical designation *Xerochrysum bracteatum.* The species is also known by the common names strawflower, paper daisy, and everlasting daisy.

The new cultivar is the product of a planned breeding program carried out by the inventor in Redland Bay, Queensland, Australia during November 2001. The objective of the breeding program was to create new cultivars having a compact bush habit, narrow leaves, and inflorescences or flower heads in a range of colors and held above the foliage on short peduncles.

The female or seed parent was the unpatented Proprietory Selection 99–20. The characteristics of the female parent are large flower heads with few white bracts, large spreading bush habit, and large broad leaves. The male or pollen parent was the unpatented Proprietary Selection 99–525. The characteristics of the male parent are large flower heads with many white bracts giving the flower a double appearance, large spreading bush, and large broad leaves.

The new cultivar was discovered and selected from the progeny of the stated cross by the inventor in October 2002 in a controlled environment in Redland Bay, Australia. The first act of asexual reproduction of the new cultivar was accomplished when vegetative cuttings were made by the inventor from the selection in October 2002 and grown in a controlled environment in Redland Bay, Australia by or under the supervision of the inventor. Horticultural examination of controlled flowerings of successive planting has shown that the unique combination of characteristics of the new cultivar are firmly fixed and are retained through successive generations of asexual reproduction.

The new cultivar has not been observed under all possible environmental conditions. The phenotype may vary significantly with variations in environment such as temperature, light intensity, fertilization levels, and day length without, however, any variance in genotype. The following observations, measurements and comparisons describe plants grown in Redland Bay, Australia under normal commercial growing conditions. The age of the plant described is 16 weeks.

SUMMARY OF THE INVENTION

The following traits have been repeatedly observed and have been determined to be basic characteristics of the new cultivar, which in combination distinguish the new cultivar as being new and distinct:

1. Clear white inflorescences
2. Compact plant habit
3. Many inflorescences per bush
4. Early flowering
5. Narrow leaf width
6. Inflorescences held above the foliage on long peduncles.

The new cultivar differs from its male parent by virtue of the new cultivar's compact plant habit and narrower leaf width, earlier flowering, more flowers per bush, and fewer bracts per flower head. Compared to the female parent, the new cultivar differs therefrom by its compact plant habit, narrower leaf width, earlier flowering and more flowers per bush.

Of the many commercial cultivars known to the present inventor, the most similar in comparison to the new cultivar is the cultivar 'REDBRAWHI', disclosed in U.S. Plant Pat. No. 12,967. In comparative testing conducted in Redland Bay, Australia, plants of the new cultivar differ from plants of the comparison cultivar in the characteristics as described in the following Table 1:

TABLE 1

| Trait | 'FLOBRASAT' | 'REDBRAWHI' |
|---|---|---|
| Leaf width | narrow | broad |
| Flower number | many | few |
| Flower size | medium | large |
| Flowering time | early | late |
| Peduncle length | long | short |

BRIEF DESCRIPTION OF THE PHOTOGRAPHS

The top photograph shows an overall view of a typical flowering plant of the new cultivar, grown in a 14 cm container for about 10 weeks after planting.

The bottom photograph shows a close up of a typical inflorescence.

The colors in the photographs show the colors as true as is reasonably possible with colored reproductions of this type. If any differences exist between the photographic color and the color values described below, the values in the detailed description are accurate.

DETAILED BOTANICAL DESCRIPTION

In the following description color references are made to The Royal Horticultural Society Colour Chart. The values are based on plant material 16 weeks old grown in Redland Bay, Queensland, Australia and the values were taken Jun. 21, 2007.

Botanical classification: *Bracteantha bracteata* 'FLOBRAELE'.

*Seed parent.*—Proprietary selection 99–20.

*Pollen parent.*—Proprietary selection 99–525.

Propagation:

*Type.*—Shoot tip cutting.

*Time and temperature to initiate roots.*—Summer, about 21 to 28 days at 20 to 25 deg. C in the greenhouse; winter, about 28 to 35 days at 15 to 20 deg. C in the greenhouse.

*Rooting description.*—Freely branching, fibrous, root density moderate, color pale brown.

Plant description:

*General appearance and form.*—Compact and bushy growth habit; upright, outwardly spreading and rounded plant form with dense foliage and inflorescences held above the foliage on long peduncles.

*Growth and branching habit.*—Freely branching with lateral branches forming at every node to produce a dense and bushy plant.

*Plant habit.*—Rounded, compact, highly branched, vigorous.

*Plant height* (*soil level to the top of a mature plant in* 14 *cm container*).—15 cm.

*Plant diameter.*—35 cm.

*Time to produce mature plants.*—After rooting, about 10 weeks are required to produce finished flowering plants in 14 cm. pots.

Branches:

*Number of branches per plant.*—83.

*Length.*—12 cm.

*Width.*—3.6 mm.

*Internode length.*—About 1.0 cm.

*Orientation.*—Upright, mounding.

*Texture.*—Slightly pubescent.

*Color.*—195D.

Foliage description:

*Leaf shape.*—Linear elliptic.

*Arrangement.*—Alternate, single, sessile.

*Length.*—About 8 cm.

*Width.*—About 1.8 cm.

*Shape at apex.*—Acute.

*Shape at base.*—Sessile.

*Margin.*—Entire.

*Color of young foliage.*—Upper surface: 138 A. Lower surface: 138 B.

*Color of mature foliage.*—Upper surface: 137B. Lower surface: 138B. Venation pattern: Pinnate.

*Venation color.*—Upper surface 137B, lower surface 147 D.

*Leaf texture.*—Upper and lower surfaces are weakly pubescent.

Inflorescence description:

*Flower type.*—Single daisy-type composite inflorescence form. Involucral bracts and disc florets arranged acropetally on capitulum.

*Natural flowering season.*—Year-round in Redland Bay, Queensland, Australia.

*Quantity of inflorescences.*—At one time, more than 35 open flowers and buds per plant.

*Bud.*—Rate of opening (from showing color to fully open flower): 14 to 21 days.

*Length.*—About 22.5 mm.

*Diameter.*—About 11.8 mm.

*Shape.*—Broadly ovoid with acute apex.

*Color.*—White, 158 C.

Inflorescence. —Depth: About 14.5 mm. Diameter: About 51.5 mm.

*Fragrance.*—There is a strong sweet vanilla-like fragrance.

*Involucral bracts.*—Quantity per inflorescence: About 72 in multiple whorls. Length: 20.5 mm. Width: 5.5 mm. Shape: Ligulate, concave. Apex: Acute. Base: Truncate. Margin: Entire. Texture: Both surfaces, smooth, glabrous, papery, satiny. Color, upper surface when opening: 158B. lower surface when opening: 159 C. upper surface, opened flower 158C. lower surface, opened flower: 158C.

*Disc florets.*—One whorl of female filiform florets surround the perimeter of the disc; the remainder of the disc is covered with bisexual disc florets. Shape: Tubular with five lobes. Length of individual floret: 7.0 mm. Width of individual floret: 1.0 mm. Quantity: 460. Diameter of mature disc: 14.5 mm. Color, immature discs: 23 B, mature discs 23B.

*Peduncle.*—Strength: Strong. Angle: Upright, erect. Length: 7 cm. Color: 195D. Texture: slightly pubescent.

Reproductive organs:

*Androecium.*—Present only on bisexual disc florets. Anther color: 23 B. Anther shape: Fused anther tube with five long thin linear anthers surrounding the style. Anther length: not able to measure accurately, too minute. Pollen color: yellow.

*Gynoecium.*—Present on both filiform and bisexual disc florets. Pistil length: About 8.5 mm. Stigma shape: bi-parted. Stigma color: 23B. Style length: About 7.0 mm. Style color: 23 B. Ovary color: No color to describe it because of its minute size.

Seed: No seed was noted on the plants observed.

Disease/pest susceptibility: Plants of the new *Bracteantha* have not been observed to be abnormally resistant to pathogens or pests common to *Bracteantha*.

Temperature tolerance: Plants have not been observed to cease flowering at the temperatures observed at Redland Bay, Queensland, Australia.

Growth retardants: No growth retardants are required for commercial production of the new variety, and none were used on the plants observed in this description.

I claim:

1. A new and distinct cultivar of *Braceantha* plant named 'FLOBRASAT', as illustrated and described.

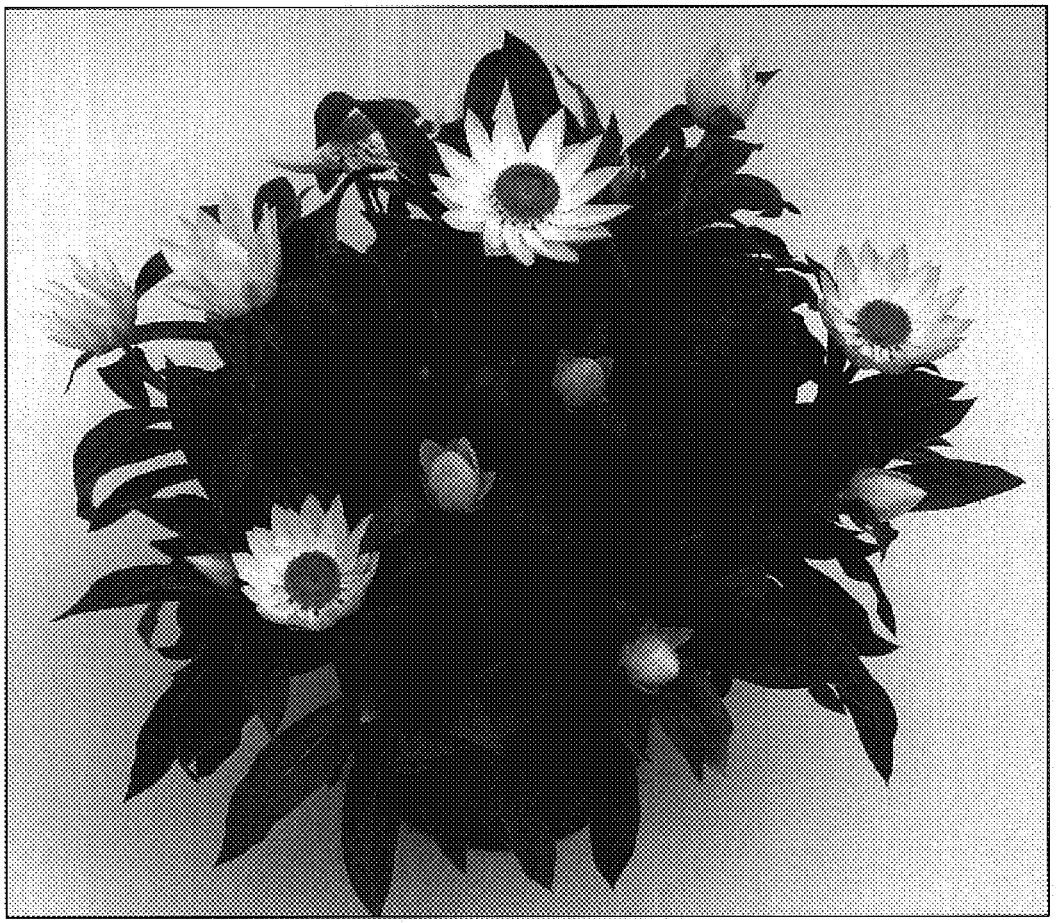
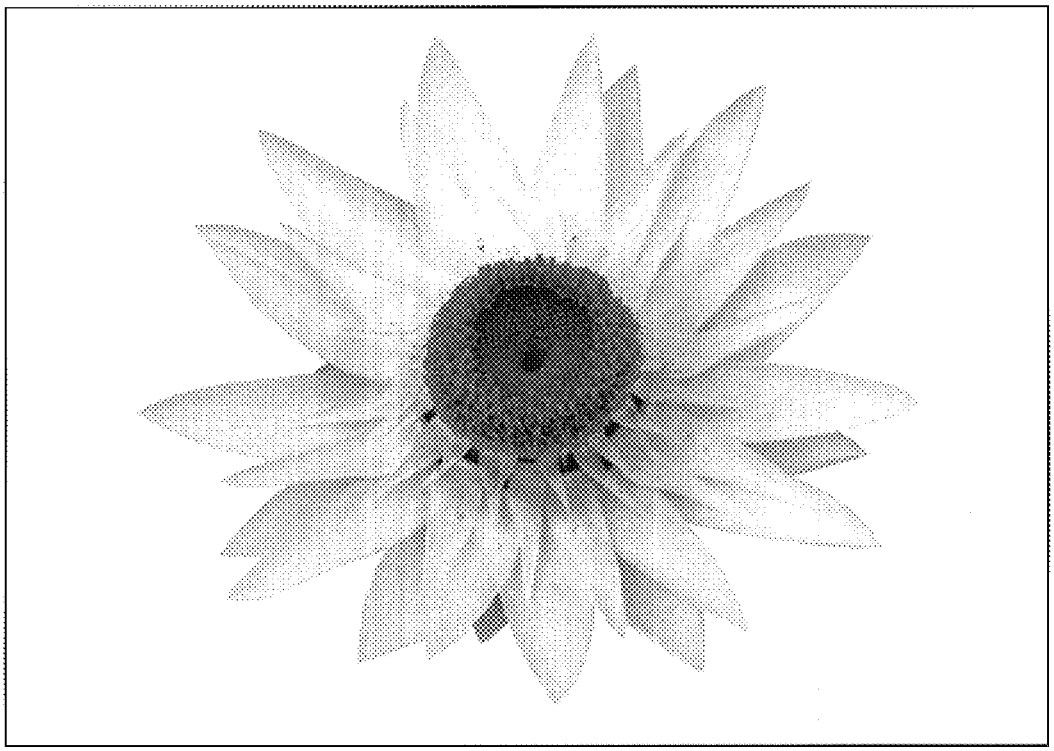

* * * * *